(12) United States Patent
Schumacher

(10) Patent No.: US 9,795,727 B2
(45) Date of Patent: Oct. 24, 2017

(54) PUMP DEVICE HAVING A DETECTION DEVICE

(71) Applicant: ECP ENTWICKLUNGSGESELLSCHAFT MBH, Berlin (DE)

(72) Inventor: Joerg Schumacher, Teltow (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 0 days.

(21) Appl. No.: 15/172,400

(22) Filed: Jun. 3, 2016

(65) Prior Publication Data

US 2017/0035953 A1 Feb. 9, 2017

Related U.S. Application Data

(63) Continuation of application No. 13/261,328, filed as application No. PCT/EP2010/007997 on Dec. 23, 2010, now Pat. No. 9,358,330.

(Continued)

(30) Foreign Application Priority Data

Dec. 23, 2009 (EP) .................................... 09075570

(51) Int. Cl.
*A61M 29/00* (2006.01)
*A61M 1/10* (2006.01)
*A61M 1/12* (2006.01)
*F04D 15/00* (2006.01)
*F04D 29/18* (2006.01)
(Continued)

(52) U.S. Cl.
CPC ........ *A61M 1/1086* (2013.01); *A61M 1/1024* (2014.02); *A61M 1/1034* (2014.02); *A61M 1/125* (2014.02); *F04D 15/0088* (2013.01); *F04D 15/0254* (2013.01); *F04D 29/043* (2013.01); *F04D 29/181* (2013.01);
(Continued)

(58) Field of Classification Search
CPC .... A61M 1/101; A61M 1/125; A61M 1/1086; A61M 1/1072; A61M 1/10
USPC .................................. 604/96.01; 600/16–18
See application file for complete search history.

(56) References Cited

U.S. PATENT DOCUMENTS 3,510,229 A 5/1970 Smith et al.
3,568,659 A 3/1971 Karnegis
(Continued)

FOREIGN PATENT DOCUMENTS

CA 1008330 A 4/1977
CA 2311977 A1 12/2000
(Continued)

*Primary Examiner* — Phillip Gray
(74) *Attorney, Agent, or Firm* — White & Case LLP

(57) ABSTRACT

The invention relates to a pump device having a pump (8) and an energy supply device (5, 18), wherein the pump has a conveying element (9, 11) which conveys a fluid by means of supplied energy, wherein the pump has a transport state and an operating state, and wherein at least one first element (9, 9a, 10, 10', 11) of the pump has a different shape and/or size in the transport state than in the operating state. The operating safety of such a pump device is increased by a detection device (12, 20, 21, 22, 23, 24, 25, 27, 28, 29) which detects whether at least the first element is in the operating state with respect to shape and/or size by means of a sensor.

20 Claims, 7 Drawing Sheets

Related U.S. Application Data

Figure 1:
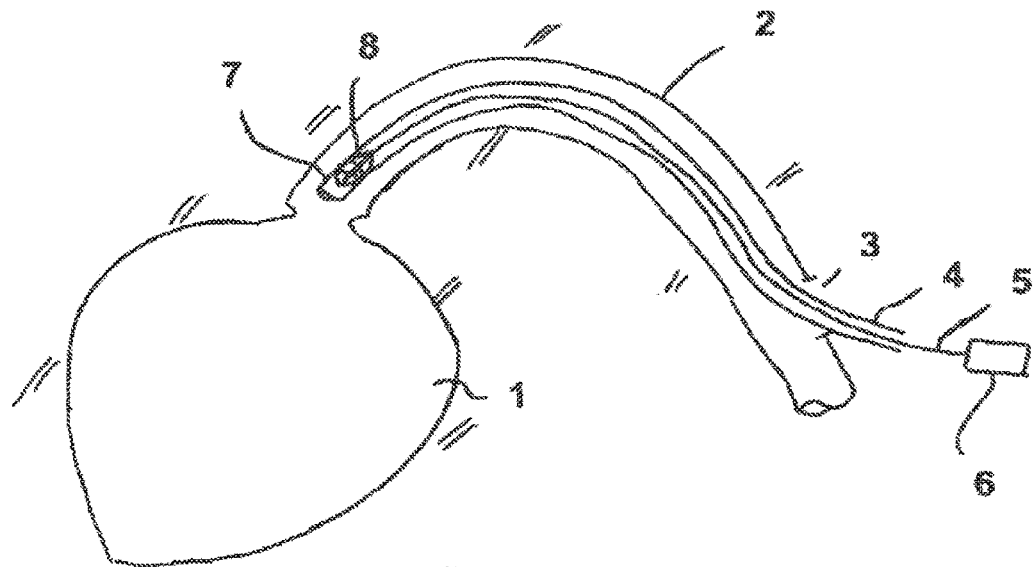

(60) Provisional application No. 61/289,656, filed on Dec. 23, 2009.

(51) Int. Cl.
  *F04D 29/24* (2006.01)
  *F04D 29/043* (2006.01)
  *F04D 15/02* (2006.01)

(52) U.S. Cl.
  CPC ....... *F04D 29/247* (2013.01); *A61M 2205/18* (2013.01); *A61M 2205/3327* (2013.01)

(56) References Cited

U.S. PATENT DOCUMENTS

| | | | |
|---|---|---|---|
| 3,802,551 A | 4/1974 | Somers | |
| 3,812,812 A | 5/1974 | Hurwitz | |
| 4,014,317 A | 3/1977 | Bruno | |
| 4,207,028 A | 6/1980 | Ridder | |
| 4,559,951 A | 12/1985 | Dahl et al. | |
| 4,563,181 A | 1/1986 | Wijayarathna et al. | |
| 4,679,558 A | 7/1987 | Kensey et al. | |
| 4,686,982 A | 8/1987 | Nash | |
| 4,747,821 A | 5/1988 | Kensey et al. | |
| 4,749,376 A | 6/1988 | Kensey et al. | |
| 4,753,221 A * | 6/1988 | Kensey ............... | A61M 1/101 415/221 |
| 4,801,243 A | 1/1989 | Norton | |
| 4,817,613 A | 4/1989 | Jaraczewski et al. | |
| 4,919,647 A | 4/1990 | Nash | |
| 4,957,504 A | 9/1990 | Chardack | |
| 4,969,865 A | 11/1990 | Hwang et al. | |
| 4,995,857 A | 2/1991 | Arnold | |
| 5,011,469 A | 4/1991 | Buckberg et al. | |
| 5,040,944 A | 8/1991 | Cook | |
| 5,042,984 A | 8/1991 | Kensey et al. | |
| 5,052,404 A | 10/1991 | Hodgson | |
| 5,061,256 A | 10/1991 | Wampler | |
| 5,092,844 A | 3/1992 | Schwartz et al. | |
| 5,097,849 A | 3/1992 | Kensey et al. | |
| 5,108,411 A | 4/1992 | McKenzie | |
| 5,112,292 A | 5/1992 | Hwang et al. | |
| 5,113,872 A | 5/1992 | Jahrmarkt et al. | |
| 5,117,838 A | 6/1992 | Palmer et al. | |
| 5,118,264 A | 6/1992 | Smith | |
| 5,145,333 A | 9/1992 | Smith | |
| 5,158,529 A | 10/1992 | Kanai | |
| 5,163,910 A | 11/1992 | Schwartz et al. | |
| 5,169,378 A | 12/1992 | Figuera | |
| 5,183,384 A | 2/1993 | Trumbly | |
| 5,191,888 A | 3/1993 | Palmer et al. | |
| 5,201,679 A | 4/1993 | Velte, Jr. et al. | |
| 5,275,580 A | 1/1994 | Yamazaki | |
| 5,373,619 A | 12/1994 | Fleischhacker et al. | |
| 5,376,114 A | 12/1994 | Jarvik | |
| 5,501,574 A | 3/1996 | Raible | |
| 5,531,789 A | 7/1996 | Yamazaki et al. | |
| 5,701,911 A | 12/1997 | Sasamine et al. | |
| 5,749,855 A | 5/1998 | Reitan | |
| 5,755,784 A | 5/1998 | Jarvik | |
| 5,776,190 A | 7/1998 | Jarvik | |
| 5,813,405 A | 9/1998 | Montano, Jr. et al. | |
| 5,820,571 A | 10/1998 | Erades et al. | |
| 5,851,174 A | 12/1998 | Jarvik et al. | |
| 5,882,329 A | 3/1999 | Patterson et al. | |
| 5,888,241 A | 3/1999 | Jarvik | |
| 5,911,685 A | 6/1999 | Siess et al. | |
| 5,938,672 A | 8/1999 | Nash | |
| 5,964,694 A | 10/1999 | Siess et al. | |
| 6,030,397 A | 2/2000 | Monetti et al. | |
| 6,058,593 A | 5/2000 | Siess | |
| 6,129,704 A | 10/2000 | Forman et al. | |
| 6,139,487 A | 10/2000 | Siess | |
| 6,152,693 A | 11/2000 | Olsen et al. | |
| 6,168,624 B1 | 1/2001 | Sudai | |
| 6,248,091 B1 | 6/2001 | Voelker | |
| 6,254,359 B1 | 7/2001 | Aber | |
| 6,302,910 B1 | 10/2001 | Yamazaki et al. | |
| 6,308,632 B1 | 10/2001 | Shaffer | |
| 6,336,939 B1 | 1/2002 | Yamazaki et al. | |
| 6,346,120 B1 | 2/2002 | Yamazaki et al. | |
| 6,387,125 B1 | 5/2002 | Yamazaki et al. | |
| 6,503,224 B1 | 1/2003 | Forman et al. | |
| 6,506,025 B1 | 1/2003 | Gharib | |
| 6,508,787 B2 | 1/2003 | Erbel et al. | |
| 6,517,315 B2 | 2/2003 | Belady | |
| 6,527,521 B2 | 3/2003 | Noda | |
| 6,533,716 B1 | 3/2003 | Schmitz-Rode et al. | |
| 6,537,030 B1 | 3/2003 | Garrison | |
| 6,537,315 B2 | 3/2003 | Yamazaki et al. | |
| 6,592,612 B1 | 7/2003 | Samson et al. | |
| 6,652,548 B2 | 11/2003 | Evans et al. | |
| 6,719,791 B1 | 4/2004 | Nusser et al. | |
| 6,860,713 B2 | 3/2005 | Hoover | |
| 6,945,977 B2 | 9/2005 | Demarais et al. | |
| 6,981,942 B2 | 1/2006 | Khaw et al. | |
| 7,022,100 B1 | 4/2006 | Aboul-Hosn et al. | |
| 7,027,875 B2 | 4/2006 | Siess et al. | |
| 7,074,018 B2 | 7/2006 | Chang | |
| 7,179,273 B1 | 2/2007 | Palmer et al. | |
| 7,393,181 B2 | 7/2008 | McBride et al. | |
| 7,467,929 B2 | 12/2008 | Nusser et al. | |
| 7,731,675 B2 | 6/2010 | Aboul-Hosn et al. | |
| 7,927,068 B2 | 4/2011 | Mcbride et al. | |
| 7,934,909 B2 | 5/2011 | Nuesser et al. | |
| 2002/0123661 A1 | 9/2002 | Verkerke et al. | |
| 2003/0135086 A1 | 7/2003 | Khaw et al. | |
| 2003/0231959 A1 | 12/2003 | Snider | |
| 2004/0044266 A1 | 3/2004 | Siess et al. | |
| 2004/0046466 A1 | 3/2004 | Siess et al. | |
| 2004/0093074 A1 | 5/2004 | Hildebrand et al. | |
| 2004/0152945 A1 | 8/2004 | Kantrowitz et al. | |
| 2004/0215222 A1 | 10/2004 | krivoruchko | |
| 2004/0215228 A1 | 10/2004 | Simpson et al. | |
| 2006/0008349 A1 | 1/2006 | Khaw | |
| 2006/0062672 A1 | 3/2006 | McBride et al. | |
| 2006/0149166 A1 | 7/2006 | Zvuloni | |
| 2006/0195004 A1 | 8/2006 | Jarvik | |
| 2008/0028114 A1 | 1/2008 | Mun | |
| 2008/0132747 A1 | 6/2008 | Shifflette | |
| 2008/0262584 A1 | 10/2008 | Bottomley et al. | |
| 2008/0306327 A1 | 12/2008 | Shifflette | |
| 2009/0060743 A1 | 3/2009 | McBride et al. | |
| 2009/0093764 A1 | 4/2009 | Pfeffer et al. | |
| 2009/0093796 A1 | 4/2009 | Pfeffer et al. | |
| 2010/0041939 A1 | 2/2010 | Siess | |
| 2010/0268017 A1 | 10/2010 | Siess | |
| 2011/0238172 A1 | 9/2011 | Akdis | |
| 2011/0275884 A1 | 11/2011 | Scheckel | |
| 2012/0039711 A1 | 2/2012 | Roehn | |
| 2012/0041254 A1 | 2/2012 | Scheckel | |
| 2012/0046648 A1 | 2/2012 | Scheckel | |
| 2012/0093628 A1 | 4/2012 | Liebing | |
| 2012/0101455 A1 | 4/2012 | Liebing | |
| 2012/0142994 A1 | 6/2012 | Toellner | |
| 2012/0184803 A1 | 7/2012 | Simon et al. | |
| 2012/0224970 A1 | 9/2012 | Schumacher et al. | |
| 2012/0234411 A1 | 9/2012 | Scheckel | |
| 2012/0237353 A1 | 9/2012 | Schumacher et al. | |
| 2012/0237357 A1 | 9/2012 | Schumacher et al. | |
| 2012/0264523 A1 | 10/2012 | Liebing | |
| 2012/0265002 A1 | 10/2012 | Roehn et al. | |
| 2012/0294727 A1 | 11/2012 | Roehn | |
| 2012/0301318 A1 | 11/2012 | Er | |
| 2012/0308406 A1 | 12/2012 | Schumacher | |
| 2013/0019968 A1 | 1/2013 | Liebing | |
| 2013/0041202 A1 | 2/2013 | Toellner | |
| 2013/0060077 A1 | 3/2013 | Liebing | |
| 2013/0066139 A1 | 3/2013 | Wiessler et al. | |
| 2013/0085318 A1 | 4/2013 | Toellner | |
| 2013/0177409 A1 | 7/2013 | Schumacher et al. | |
| 2013/0177432 A1 | 7/2013 | Toellner et al. | |

(56) References Cited

U.S. PATENT DOCUMENTS

| | | |
|---|---|---|
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 A1 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 69017784 T2 | 11/1995 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69427390 T2 | 9/2001 |
| DE | 100 59 714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0480102 A1 | 4/1992 |
| EP | 0560000 A2 | 9/1993 |
| EP | 0629412 A2 | 12/1994 |
| EP | 0768091 A1 | 4/1997 |
| EP | 0884064 A2 | 12/1998 |
| EP | 0916359 A1 | 5/1999 |
| EP | 1019117 A1 | 7/2000 |
| EP | 1066851 A1 | 1/2001 |
| EP | 1114648 A2 | 7/2001 |
| EP | 914171 | 10/2001 |
| EP | 1337288 A1 | 8/2003 |
| EP | 951302 | 9/2004 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| RU | 2229899 C2 | 6/2004 |
| WO | WO-9202263 A1 | 2/1992 |
| WO | WO-9302732 A1 | 2/1993 |
| WO | WO-9303786 A1 | 3/1993 |
| WO | WO-9314805 A1 | 8/1993 |
| WO | WO-9401148 A1 | 1/1994 |
| WO | WO-9405347 A1 | 3/1994 |
| WO | WO-9409835 A1 | 5/1994 |
| WO | WO-9420165 A2 | 9/1994 |
| WO | WO-9523000 A2 | 8/1995 |
| WO | WO-9618358 A1 | 6/1996 |
| WO | WO-9625969 A2 | 8/1996 |
| WO | WO-9744071 A1 | 11/1997 |
| WO | WO-9853864 A1 | 12/1998 |
| WO | WO-9919017 A1 | 4/1999 |
| WO | WO-0027446 A1 | 5/2000 |
| WO | WO-0043054 A2 | 7/2000 |
| WO | WO-0062842 A1 | 10/2000 |
| WO | WO-0107760 | 2/2001 |
| WO | WO-0107787 | 2/2001 |
| WO | WO-0117581 A2 | 3/2001 |
| WO | WO-0183016 | 11/2001 |
| WO | WO-03057013 | 7/2003 |
| WO | WO-03103745 | 12/2003 |
| WO | WO-2005002646 A1 | 1/2005 |
| WO | WO-2005016416 A1 | 2/2005 |
| WO | WO-2005021078 A1 | 3/2005 |
| WO | WO-2005030316 A1 | 4/2005 |
| WO | WO-2005032620 A1 | 4/2005 |
| WO | WO-2005081681 A2 | 9/2005 |
| WO | WO-2006020942 A1 | 2/2006 |
| WO | WO-2006034158 A2 | 3/2006 |
| WO | WO-2006133209 A1 | 12/2006 |
| WO | WO-2007003351 A1 | 1/2007 |
| WO | WO-2007103390 A2 | 9/2007 |
| WO | WO-2007103464 A2 | 9/2007 |
| WO | WO-2007112033 A2 | 10/2007 |
| WO | WO-2008017289 A2 | 2/2008 |
| WO | WO-2008034068 A2 | 3/2008 |
| WO | WO-2008054699 A2 | 5/2008 |
| WO | WO-2008106103 A2 | 9/2008 |
| WO | WO-2008116765 A2 | 10/2008 |
| WO | WO-2008124696 A1 | 10/2008 |
| WO | WO-2008137352 A1 | 11/2008 |
| WO | WO-2008137353 A1 | 11/2008 |
| WO | WO-2009015784 A1 | 2/2009 |
| WO | WO-2010133567 A1 | 11/2010 |
| WO | WO-2013034547 A1 | 3/2013 |
| WO | WO-2013092971 A1 | 6/2013 |
| WO | WO-2013093001 A2 | 6/2013 |
| WO | WO-2013093058 A1 | 6/2013 |

* cited by examiner

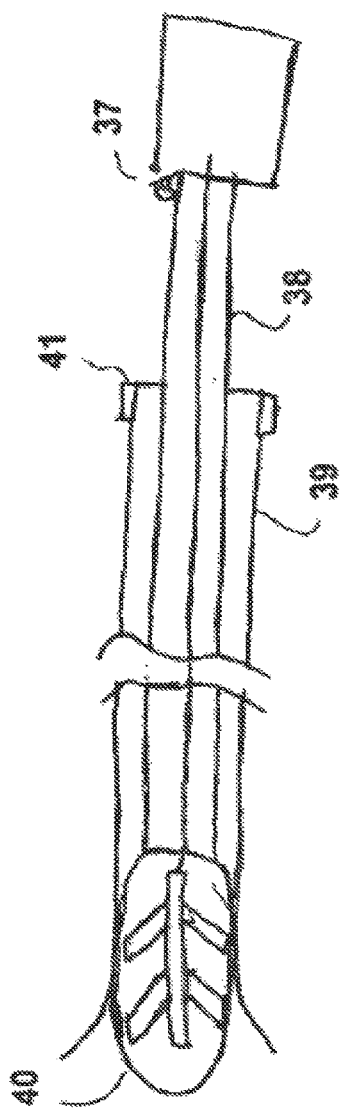
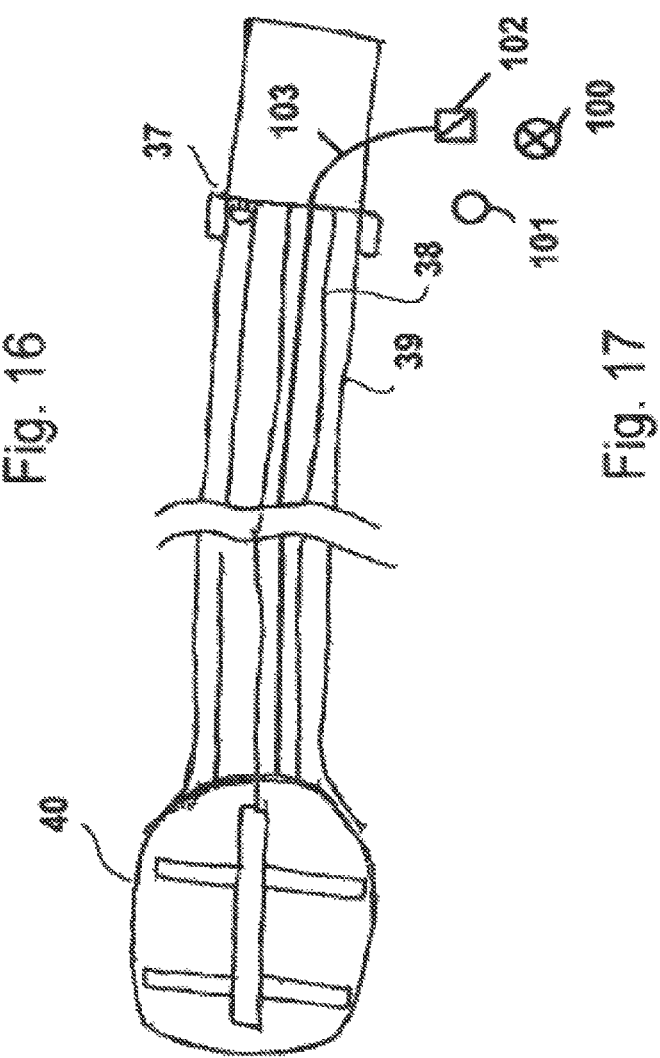

PUMP DEVICE HAVING A DETECTION DEVICE

CROSS-REFERENCE TO RELATED APPLICATIONS

This application is a continuation of U.S. patent application Ser. No. 13/261,328, which entered the national stage on Aug. 16, 2012 and which is a United States National Stage filing under 35 U.S.C. §371 of International Application No. PCT/EP2010/007997, filed Dec. 23, 2010, which claims the benefit of U.S. Provisional Patent Application No. 61/289,656, filed Dec. 23, 2009, and European Patent Application No. 09075570.3, filed Dec. 23, 2009, the contents of all of which are incorporated by reference herein in their entirety. International Application No. PCT/EP2010/007997 was published under PCT Article 21(2) in English.

The invention is in the field of mechanical engineering and precision engineering and relates to a pump device.

Pumps are used for conveying fluids, in particular liquids, and are known in a variety of variants. Pumps are particularly interesting for many applications which either have a particularly small construction or whose design is changeable to be taken to a place of deployment with difficult access in a transport state, wherein an expanded state or an operating state can afterward be established in which individual elements of the pump have a different shape and/or size than in the transport state.

Examples for such pumps are expandable catheter pumps which are introduced into a patient's body through a blood vessel and can be inserted up to and into a ventricle and can be expanded there.

For this purpose, an expanding of a rotor of the pump and of a housing typically takes place. The rotor usually carries one or more impeller blades which can be radially compressed and expanded alone or together with a hub. For this purpose, conveyor blades can, for example, be fastened flexibly or pivotably to a hub or can be configured as compressible by the manufacture as a foam body. Such conveyor blades occasionally also have portions made from a memory alloy such as nitinol which has super-elastic properties and temperature-dependent shape properties. A corresponding rotor is then radially compressible with a small force and erects itself independently again to its original shape at a suitable temperature after the removal of the compression force.

Principles are also known in accordance with which a corresponding pump is actively erected/expanded by actuation from the outside after the transport to the place of deployment (WO 94/05347 A1). Such constructions, however, require corresponding actuation devices and elements for transferring such an actuation, which requires an increased electric, pneumatic or mechanical effort.

Pump principles are also known in which conveyor blades of a rotor are erected by the fluid counter-pressure on operation with growing speed of the rotor up to an operating state in which the rotor is extended to a maximum in the radial direction.

All the named principles share the feature that an expansion of the pump elements is initiated or made possible after the taking or the pump to the place of deployment, but that the reaching of the completely expanded state (this is advantageously the operating State) is not absolutely certain. There is thus the risk that the pump does not reach the operating state at all or only reaches it in part despite a corresponding actuation. This contains a great danger, in particular on the deployment of such pumps in the biological sector, since either body fluids such as blood are damaged on the putting into operation of the pump or pump elements can get into a body fluid such as blood on damage to the pump.

This can take place, for example, if a pump rotor is set into rotation without it having its operating shape or without the housing surrounding it already being expanded to the desired diameter. In this case, impeller blades may break or may be operated in an unwanted manner in the transport state so that the rotor develops too high a speed due to a fluid resistance which is too low and damages components of the blood or of another body fluid. If the speed is controlled or regulated, the pump would possibly work with insufficient output.

It is the underlying object of the present invention against the background of the prior art to configure a pump device such that disadvantages by an operation of the pump are avoided in the compressed state or in a not sufficiently expanded state.

The object is achieved in accordance with the invention by the features of claim 1.

Provision is made in this respect that the pump device has a pump and an energy supply device, wherein the pump has a conveying element which conveys a fluid by means of a supplied energy, wherein the pump has a transport state which is for example a compressed or folded state and an expanded respectively unfolded state, and wherein at least one first element of the pump has a different shape and/or size in the transport state than in the operating state. In this respect, a detection device is moreover provided which detects whether at least the first element is located in the expanded state with respect to shape and/or size.

The first element has a different shape and/or size in the transport state than in the expanded state or in the operating state so that the pump has deformation possibilities and can be adapted to a transport path to be passed through to reach a place of deployment. The first element can, for example, be an impeller blade, a rotor or a pump housing.

Provision can, for example, be made that at least one first element at least partly comprises an elastically deformable, in particular compressible and expandable, material.

The at least one first element can thereby perform the change from the transport state into the expanded state by elastic deformation such as bending, compression, extraction or similar effects.

Such a pump can, for example, be pushable through a hose system, tubular system or channel system in that it is first reduced in size by radial compression and is later expanded again at the place of deployment.

Such principles are in particular realized in medically used micropumps in which the pump itself, and optionally the housing, are radially compressed for transport.

It is sensible to ensure that the first element has reached the expanded state before the pump is put into operation. The first element can, for example, be a rotor of the pump having at least one impeller blade, with the rotor only reaching the required pump performance when it has expanded correspondingly. If the rotor is surrounded by a housing, it must be ensured that the housing is expanded before the rotor is put into operation. The detection device can accordingly be equipped with a sensor and monitor the expanded state of the housing and/or of the rotor or of an impeller blade. This can be done, for example, in that the detection device contains a strain gage as the sensor which is fastened to an impeller blade or a position sensor which can, for example, monitor the relative position of the impeller blades toward a hub.

If such a pump is taken into operation too soon without the expanded state having been reached, there would be a risk that the impeller blades would catch at the pump housing or at other positions and might break; in every case, however, the pump is decelerated.

It can also take place that the rotor does not work correctly and that its conveying performance is not sufficient due to an insufficient expansion of the rotor.

The energy supply device can advantageously be configured as a mechanical drive and the conveying element can be configured movable and drivable by means of the drive. The typical case is thus given by a rotationally drivable pump rotor having impeller blades.

Other pump function principles are, however, also conceivable, for example having an alternatingly expanded and compressed balloon element which intermittently displaces fluid out of a chamber and thus conveys it. Pump principles are moreover conceivable without moving parts in which the conveying element, for example, generates an electric or magnetic field which acts on a fluid which has corresponding material parameters to be able to be conveyed by corresponding field effects.

It can also be sensible with such non-moved conveying elements to detect their expanded state.

A conveying element can advantageously be inflatable, bendable, pivotable or elastically compressible and expandable. This is, for example, possible in that the conveying element comprises wholly or partly an elastic foam or in that an elastic wire frame is provided over which a Membrane is spanned for forming an impeller blade, wherein the frame is elastically compressible in the radial direction and automatically adopts the original shape on the removal of a compression force. A corresponding impeller blade can also contact the hub as an expandable or bendable body and only be set up by the fluid counter-pressure being adopted at the start of operation.

A likewise compressible housing of the pump can also be provided in addition to a conveying element or to a rotor.

In this case it is particularly important that both the conveying element, for example a rotor, and the pump housing are set into the expanded state accordingly before the putting into operation. This can be done either automatically by the above-named effects when the pump is kept radially together on transport and the holding together is cancelled after the transport. This can, for example, be realized in that the pump is conducted in a hollow catheter during transport and is pushed out of the hollow catheter after the transport or at the end of the transport so that the radial holding force is removed outside the hollow catheter and the pump automatically elastically expands.

An active expanding can, however, also be provided by a corresponding actuation device such as small levers or other apparatus which engage at the rotor and the housing.

Provision is advantageously made that the detection device changes a signal state when the first element reaches the expanded state. The state of the pump can thus be actively communicated to a person operating the pump. The State can, for example, be communicated by an optical signal or by an acoustic signal.

Provision can also be made that the detection device emits a signal as long as the expanded state is not reached. The corresponding signal can thus serve as a warning signal that the pump may not yet be taken into operation.

If a signal is only output when the expanded state is reached, it is thereby ensured that, on a defect of the detection device, the pump is not put into operation for reasons of safety as long as no signal is output, even if the pump should actually have reached the expanded state with a defective sensor.

Provision can also be made that the detection device blocks the energy supply device as long as the expanded state is not reached. It is thus ensured automatically and without the intervention of an operator that the pump is not taken into operation long as the expanding of the expandable elements is not confirmed.

Provision can also advantageously be made that the detection device monitors the load of the energy supply device in operation and determines by Comparison with a reference value or a reference pattern whether the operating state has been reached.

The sensor of the detection device can thus also be arranged remote from the pump, for example in the proximity of the energy supply device, in order to monitor from there whether a conclusion can be drawn on an increased or modified resistance in pump operation due to an irregular behavior of the energy supply device. In contrast to this, provision can also be made that the detection device has a sensor which is arranged directly at the pump.

The elements of the pump can be directly monitored considerably more easily there if corresponding sensors such as strain gages are provided. It is also possible to determine, independently of the operation of the pump, whether it has already reached the operating state, i.e. has been expanded accordingly. The shape of the individual impeller blades can, for example, be monitored by attached strain gages or the angle between the impeller blades and the hub can be monitored when the impeller blades are angled from the hub in the course of an expansion.

An electrical resistance can, for example, also be monitored which corresponds to a current path from the pump housing over the impeller blades and the hub when the impeller blades or other parts of the rotor should not contact the pump housing in the expanded state and the resistance is thus high, whereas a contact between the pump housing and other parts of the pump is present in the compressed state so that the electrical resistance is reduced in this state.

An electrical capacitance between the pump housing and parts of the rotor or the total rotor can also be monitored in a similar manner, with the capacitance being influenced by the spacing between these components.

An inductance of the housing or of the rotor can also be monitored, with the inductance being influenced by the shape of the housing or rotor. When the housing or the rotor, for example, includes a framework of metal, for example nitinol, which (hyper-)elastically deformes on the change from the transport state into the expanded state, the inductance of the housing or of the rotor is also changed in dependence on the extent of the electrically conductive framework components. The change in this inductance can be detected, for example, by monitoring the reactance of the housing or of the rotor. The housing could also, for example, have an elastically deformable electric conductor wound around it which changes its resistance on the change from the transport state into the expanded state and furthermore changes the inductance since it is arranged in the manner of a coil.

A further variant can provided that an additional conductive path, for example a wire or a plurality of mutually contacting wires made from electrically conductive material is introduced into the pump and is cut or torn, i.e. interrupted, by an expansion movement so that, on the monitoring of the passage resistance of the path, a change occurs when it is interrupted. Such a wire or conductive path can, for example, completely surround the pump in the compressed state of the pump and be arranged around it, in particular spanned around it.

Provision can also be made that the monitored path which surrounds the pump or elements of the pump and is not conductive in the compressed state only becomes conductive by the expansion due to the displacement of a conductor.

An electric conductor can, for example, be integrated into the catheter for transferring the signal from the pump head to the proximal catheter section.

In this sense, a pump device having the following features is also proposed as a separate invention:

a pump device having a pump head and a catheter, wherein the catheter has a proximal end positionable outside a human body or the body of an animal and a distal end which is located toward the pump head, wherein the pump head has a mechanically movable pump member and an energy supply device is provided in the form of a flexible shaft for driving the pump member, said energy supply device extending from the proximal end to the distal end of the catheter, wherein the catheter has an additional electric conductor and/or a light guide which extends from the proximal end of the catheter to the distal end of the catheter.

It is possible for the first time in this respect that, with a mechanically driven pump, additional electrical signals can be transferred from the pump head to the proximal end which is located outside the human body/body of an animal and at which a medical operator can stand. It hereby becomes possible, for example, to exercise control functions to ensure or observe an ensuring of the correct function.

Electric signals can be transferred from the pump head and/or an electric signal can be conducted via a light guide to the pump head, can be reflected there in dependence on the expanded state, for example by the first element, and can be conducted to the proximal end of the light guide at the outside of the body. For this purpose, for example, parts of the first element can be mirror-coated.

A further embodiment of the invention can provide that the sensor monitors a holding device which compresses the pump and which is expandable or removable from the pump.

The end of a hollow catheter in which the pump is accommodated during a transport procedure can, for example, be provided as the holding device, with the pump being compressed by the surrounding hollow catheter until it is pushed out of the hollow catheter after being taken to the place of deployment, for example with the aid of a drive shaft or a further pulling force or catheter hose as a pushing tool. After the pump has been pushed out of the hollow catheter, the compressive holding force of the hollow catheter is removed so that the pump elements can elastically expand. This procedure can additionally be assisted by further measures such as a slow rotation of the pump rotor or a manipulation by additional pulling or pushing elements.

A sensor can be provided at the end of the hollow catheter which signals that the pump has been completely pushed out of the hollow catheter. It is thus ensured with a certain security that the pump has automatically expanded.

Different ones of the named and above-described sensors can also be combined with one another and logically connected to acquire a higher security with respect to whether the pump has actually been expanded before it is put into operation.

Figure 2:
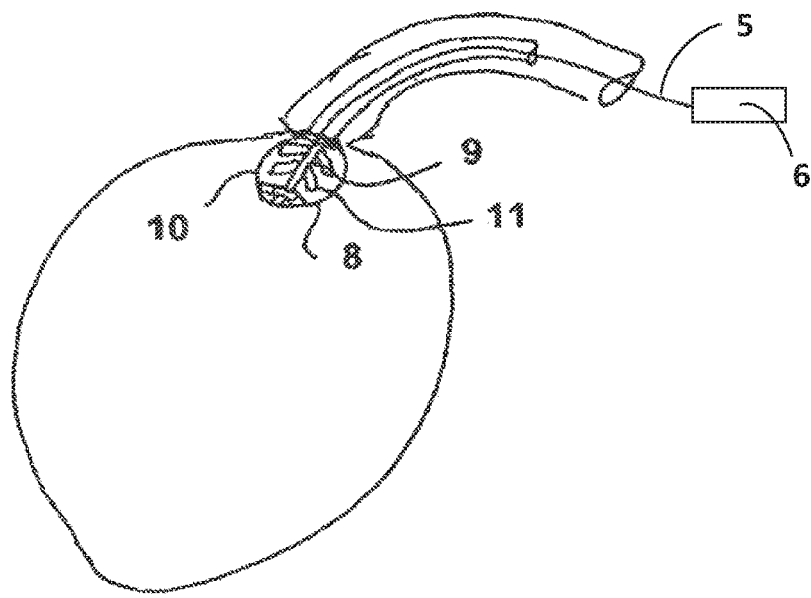
Figure 3:
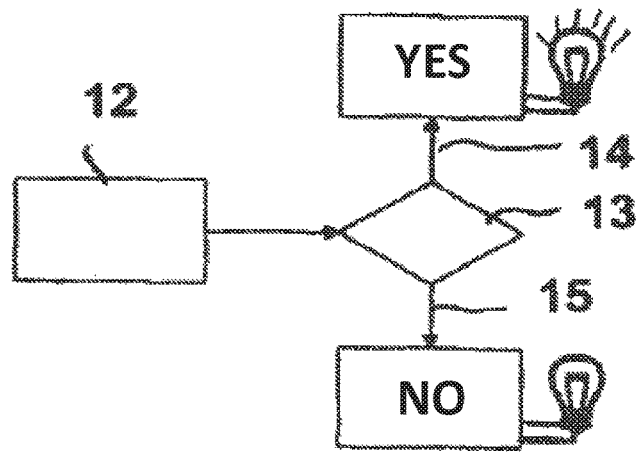
Figure 4:
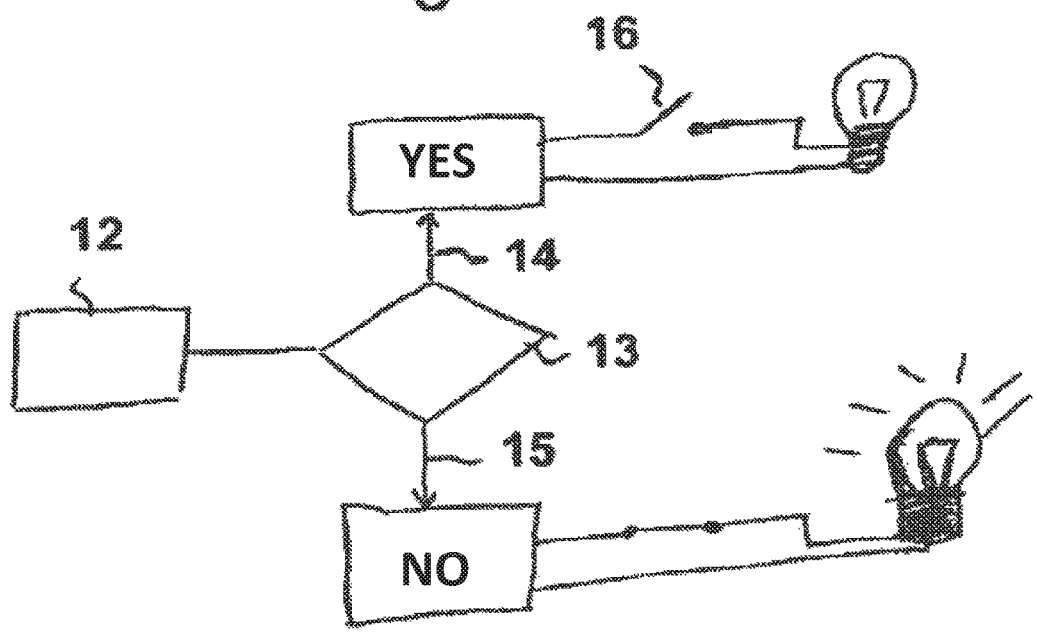
Figure 5:
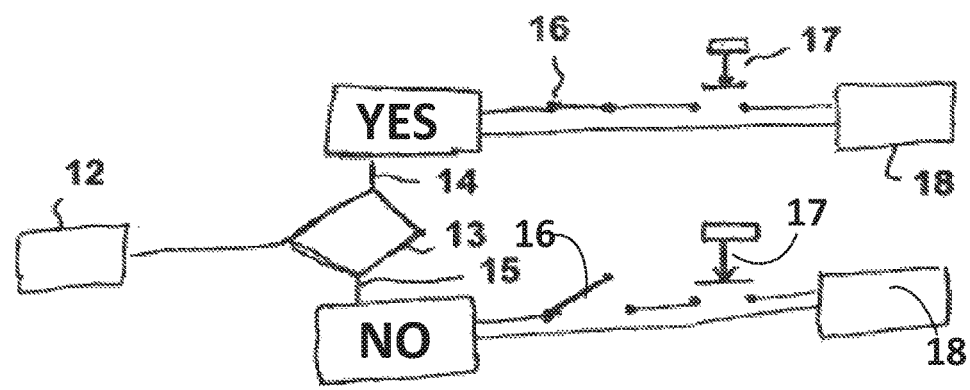
Figure 6:
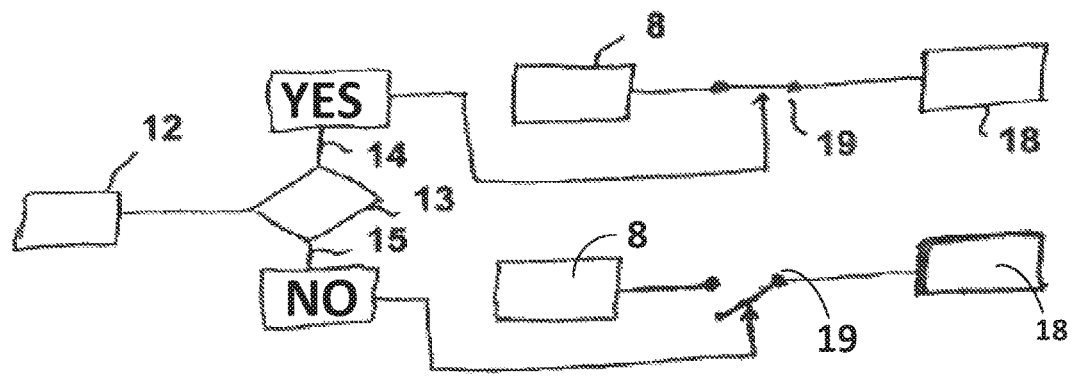
Figure 7:
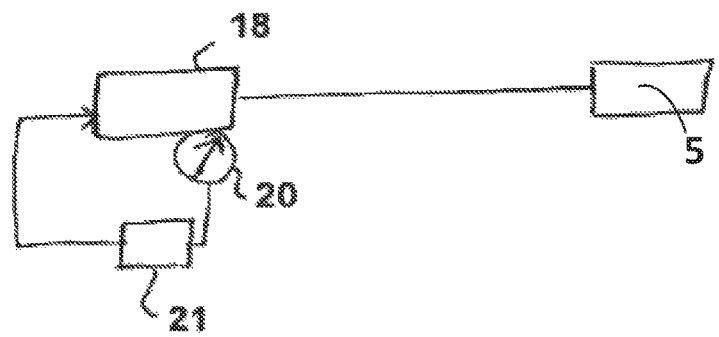
Figure 8:
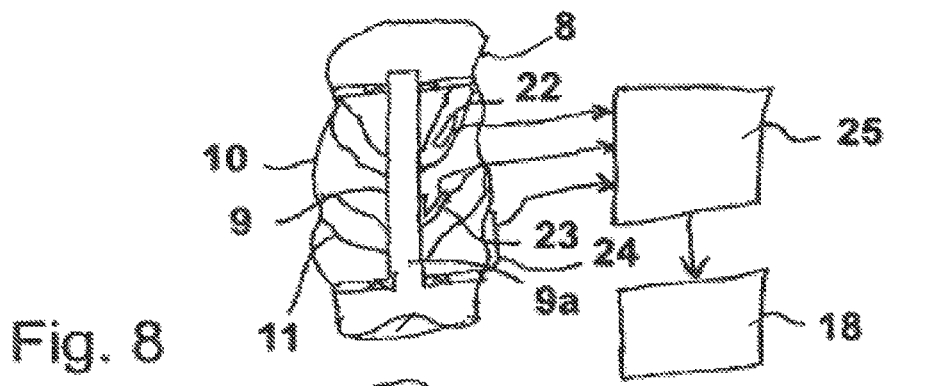
Figure 9:
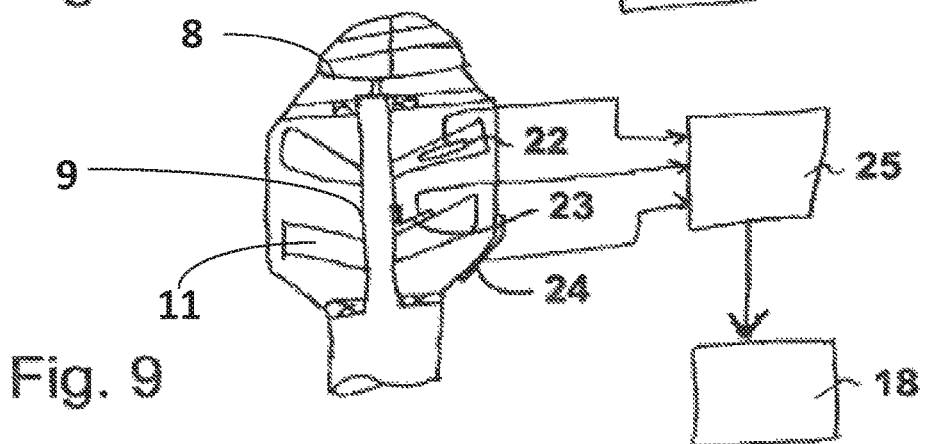
Figure 10:
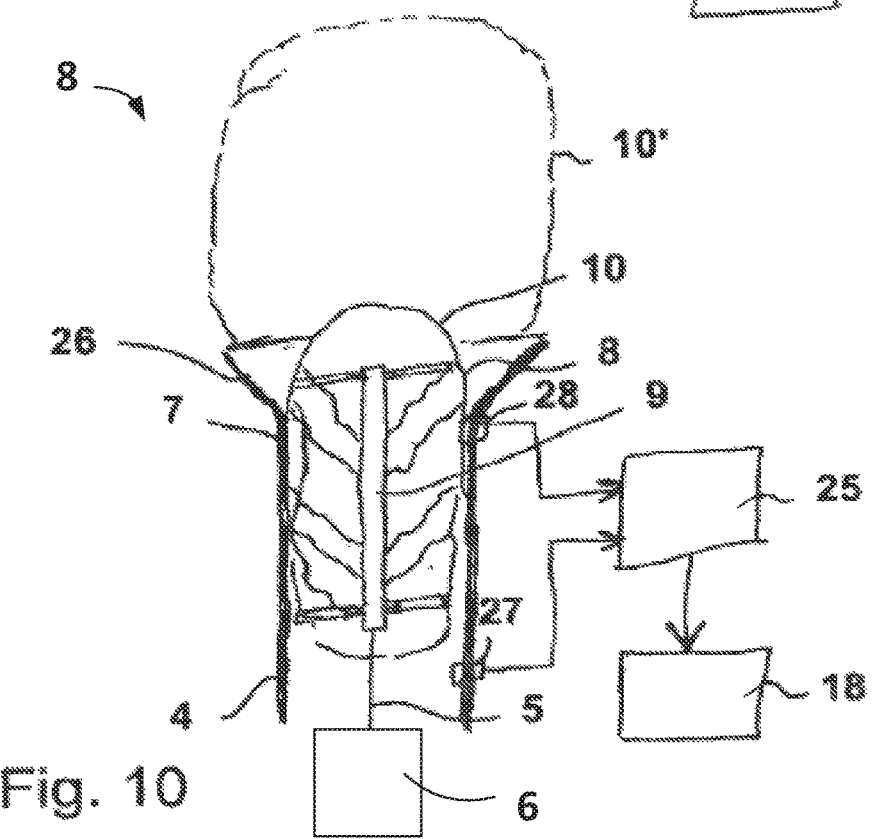
Figure 11:
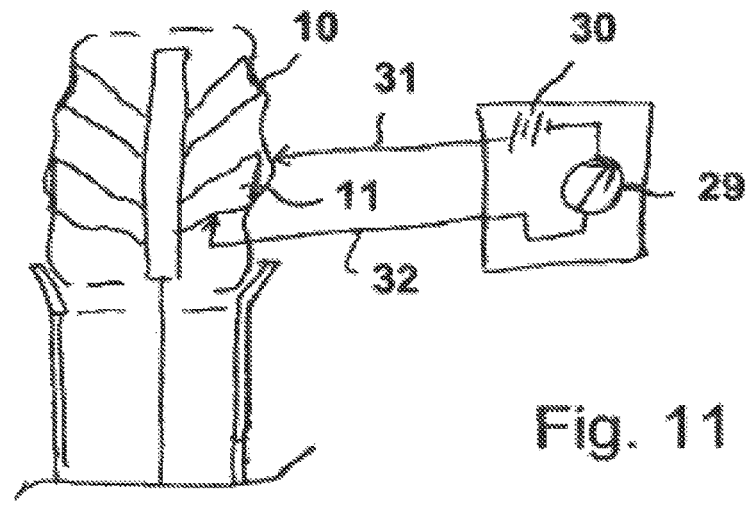
Figure 12:
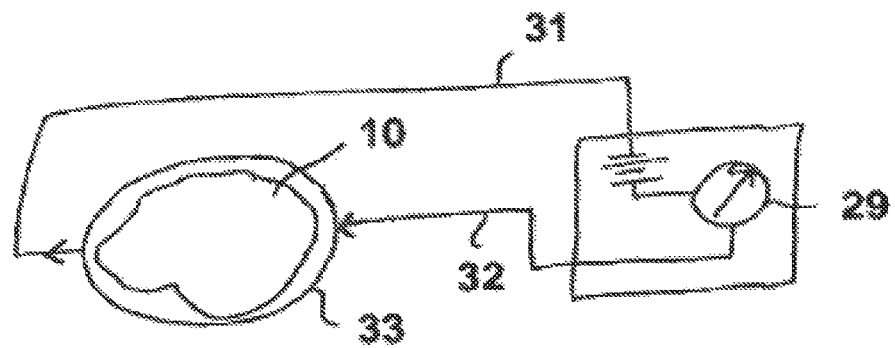
Figure 13:
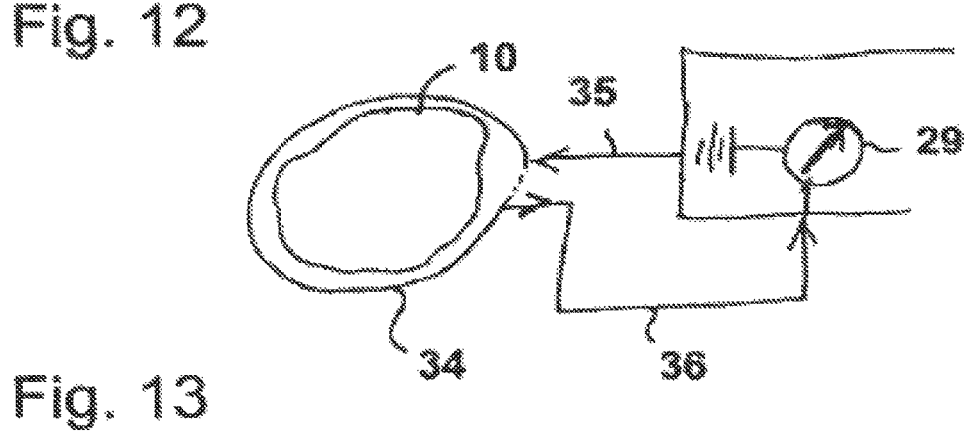
Figure 14:
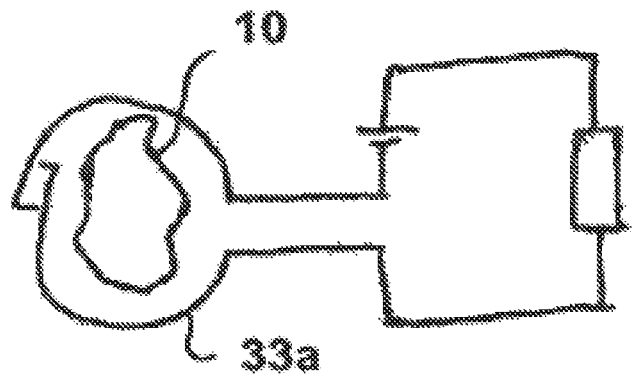
Figure 15:
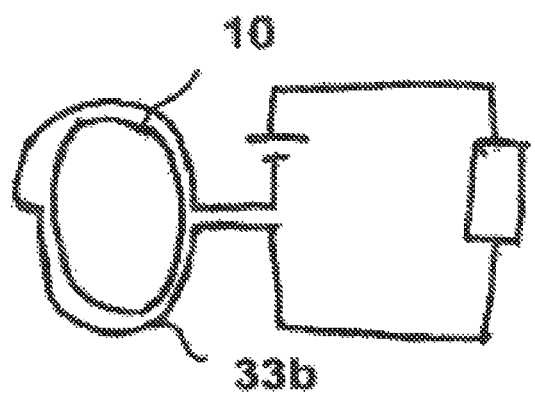

The invention will be shown and subsequently described in the following with reference to an embodiment in a drawing. There are shown FIG. 1 schematically, a heart catheter pump on being pushed through a blood vessel into a ventricle;

FIG. 2 the pump of FIG. 1 after the reaching the ventricle and after the expanding;

FIG. 3 a first signal processing of detector signals;

FIG. 4 a second processing of detector signals;

FIG. 5 a processing of detector signals with an additional control of the drive device;

FIG. 6 a signal processing in which the connection between the drive device and the pump is interrupted from case to case;

FIG. 7 a detection device which is arranged at the drive device;

FIG. 8 a pump in compressed form;

FIG. 9 the pump of FIG. 8 in expanded form;

FIG. 10 a pump which is positioned in compressed form in a ventricle;

FIG. 11 a detection device of a pump which measures an electric resistance;

FIG. 12 a detection device which measures the resistance of a wire spanning around a pump;

FIG. 13 a detection device similar to that of FIG. 12 with an interrupted conductor;

FIG. 14 a pump in the compressed state, surrounded by a non-conductive path;

FIG. 15 the pump of FIG. 14 in an at least partly expanded state with a closed conductor path;

FIG. 16 schematically, a pump in a longitudinal section whereas it is compressed in a hollow catheter at the end of said hollow catheter; and FIG. 17 the pump of FIG. 16 outside the catheter in an expanded state.

FIG. 1 schematically shows a ventricle 1 into which a blood vessel 2 opens through which a hollow catheter 4 is introduced by means of a sluice 3. The hollow catheter has a rotating shaft 5 in its hollow space which is drivable at high revolutions, typically more than 10,000 revolutions per minute, by means of a motor 6.

The shaft 5 drives a pump 8 at the distal end 7 of the hollow catheter, said pump being compressed by the hollow catheter in the still compressed state at the end of the hollow catheter in the representation of FIG. 1.

The pump can, for example, be pushed out of the end of the hollow catheter 4 into the ventricle 1 by means of the shaft 5 or by means of further elements not shown. The state which thus arises is shown in FIG. 2 where the pump 8 is shown in the expanded form. A rotor 9 is thus shown in schematic form in the interior of a pump housing 10.

The rotor 9 has impeller blades 11 which project radially from a hub and which are rolled up, folded up or otherwise compressed in the compressed state of the pump.

In the design shown in FIG. 2, the pump 8 is ready for operation, i.e. it is in the expanded state and can convey blood by rotation of the rotor. In FIG. 1, in contrast, the pump 8 is shown in the transport state, i.e. it is compressed within the hollow catheter 4.

The transition from the compressed form of the pump to the expanded form can take place, for example, when the outer compressive forces are removed, by the inherent elasticity of the pump housing 10 and of the rotor 9.

Additional manipulation elements can, however, also additionally be provided such as pulls which extend along the hollow catheter 4 at its outer side or in the lumen and which can effect the folding open and expanding of the pump by the application of a pulling force or pressure onto the pump.

The pump can ultimately, for example, also be expanded in that the rotor is rotated slowly so that, for example, the impeller blades 11 are erected by the fluid counter-pressure of the blood which is trapped in said impeller blades.

The pump housing 10 can likewise be inflated by a slight overpressure which is generated by the rotor.

It is also conceivable to equip the pump with inflatable hollow spaces, in that, for example, the pump housing 10 is produced as a double-wall balloon and the rotor likewise has inflatable hollow spaces both in the impeller blades and, optionally in the hub, wherein the individual elements of the pump in this case have to be connected to a controllable pressure source via hydraulic or pneumatic lines. The named components can also comprise a foam which adopts its expanded form automatically after the removal of compressive forces.

It is decisive for an increased operating security in this respect that the expanded state of the pump is also checked and detected so that, for example, a treating physician can decide whether the pump can be put into operation.

For this purpose, different kinds of sensors can be provided which will be described in more detail further below.

It is shown with reference to FIG. 3 how a signal coming from such a sensor can be processed.

The sensor is marked by 12 in FIG. 3. It delivers a signal to a decision-making device 13 which decides on the basis of the sensor signals whether the pump is expanded or not or whether a specific element of the pump is expanded. If the expanded state has been reached (Yes), the signal path 14 is selected. If the expanded state has not been reached (No), the signal 15 is terminated. Depending on what the state of the pump is, a signal, in FIG. 3, for example, a light signal, is output when the expanded state has been reached or it is suppressed as long as the expanded state has not yet been reached.

The light signal arrangement can also be exactly the opposite so that a light signal is output as long as the expanded state has not been reached and it is extinguished as soon as the expanded state has been reached.

Instead of light signals, other types of signals can also be emitted such as acoustic signals.

It is shown in FIG. 4 that, in accordance with the same structure as in FIG. 3, a switch 16 to a signal element is interrupted on the reaching of the expanded state and a corresponding adoption of the signal state 14 (Yes), whereas the same switch element or also a different switch element is closed when the signal state 15 (No) is adopted.

Different elements which achieve specific desired effects can also be connected to the corresponding switches 16 instead of a signal element.

A constellation is shown in FIG. 5 in which a further switch 17 is provided in series with a switch 16 which is actuated in dependent on the signal, and said further switch is actuable by hand and results in the actuation of the drive 18 of the pump This has the consequence that in the event that the expanded state is reached (Yes), the signal 14 is output and the switch 16 is closed. The drive can thus be switched on by actuating the switch 17.

As long as the signal for the reaching of the expanded state has not been given (No), shown by the signal 15, the switch 16 remains open, as shown in the lower half of FIG. 6, so that the switch 17 can admittedly be actuated, but the drive 18 is thereby means of the sensor 12 or by meals of its signal processing.

In FIG. 6, a variant of the circuit shown in FIG. 3 is described in which a switch 19 which permits or blocks the transfer of energy from the drive 18 to the pump 8 is actuated by the signal processing. If the expanded state of the pump has been reached, characterized by the signal 14, the switch 19 is closed and the energy can move from the drive 18 to the pump. As long as the expanded state has not been reached, characterized by the signal 15, the switch 19 remains open and the effect of the drive does not reach the pump.

The examples for a drive control of FIGS. 5 and 6 can also be combined with a signal processing in accordance with the examples of FIGS. 1 to 4 such that both a signal which can be perceived outside the body appears or is extinguished and the energy supply of the drive device is switched free or blocked.

The switch 19 can, for example, be configured as an electric switch, but also as a pneumatic or hydraulic valve which is arranged in the powertrain.

It can also be a coupling which blocks the transmission of the torque via the shaft in that the coupling changes into the disengaged state in which no torque is transmitted.

FIG. 7 schematically shows the arrangement of a sensor 20 directly at the drive 18, with the sensor 20, for example, measuring the current flowing through the drive or measuring the load of the drive in another manner.

If the pump is not yet in the expanded state, the load of the drive becomes higher than in the expanded state since the pump is either unable to be moved at all or can only be moved with large friction losses.

The load is detected by the sensor 20 and is compared by means of a processing device 21 as part of the detection device with reference values or reference patterns, with the device 21 being able to influence the drive 18, for example being able to switch it off when it is detected that the expanded state has not yet been reached.

The sensor 20 is in this case typically arranged remote from the pump and closer to the drive, i.e. in the example shown in FIGS. 1 and 2, in the proximity of the electric motor 6 or its current source. Provision can also be made in this respect that the corresponding motor, either an electric motor or, for example, also a microturbine, can be arranged at the distal end of the hollow catheter 4 so that in this case the sensor 20 is also arranged there.

In FIG. 8, a pump 8 is shown schematically in the compressed state with a folded-together housing 10 and a rotor 9 whose impeller blades 11 are likewise compressed, for example folded into the hub 9a.

Strain gages 22, 23, 24 are shown, with the strain gage 22 being arranged on an impeller blade, the strain gage 23 in the starting region of an impeller blade at the hub 9a and the strain gage 24 outside at the housing 10.

The strain gages are in each case stuck on and register changes in shape and size of the carrier material. They are each connected via lines to an evaluation device 25 which registers the extent of shape changes during the expansion process of the pump. The signals of the individual strain gages can be combined, with the logic of this combination being able to have a different design. The reaching of the operating state can, for example, only be signaled when all the strain gages report an expansion of the respective element monitored by them or when at least two of these elements or even already a single element reports the reaching of the expanded state. A signal to the drive 18 is accordingly output.

The pump of FIG. 8 is shown in an expanded state in FIG. 9.

FIG. 10 shows the end 7 of a hollow catheter 4 in which a pump 8 is compressed. The pump 8 is connected to the motor 6 by means of the shaft 5 through the hollow catheter 4. Both the housing 10 and the rotor 9 having the impeller blades are compressed.

The housing 10' is shown by dashed lines in a state which is reached after the expansion of the pump. An introduction cone 26 is moreover shown via which the pump 10 is moved in and is radially compressed there on the pulling into the hollow catheter 4 before the removal from the patient body.

Two sensors 27, 28 are provided within the hollow catheter 4 which signal whether the pump is in the region of the hollow catheter represented and monitored by them or whether it has already been moved out of it. In the representation of FIG. 10, the region of the sensor 27 has already been passed by the pump, but the sensor 28 still signals that the pump is compressed in this region. After the moving out of the hollow catheter, the sensor 28 will report that it is free and that the pump has been moved out of the hollow catheter and has thus expanded. The corresponding signals are processed in a signal processing device 25 and are optionally forwarded to the drive 18.

FIG. 11 shows a sensor 29 which is designed as a resistance measuring sensor and which is connected in series with a current sourced 30 and is connected via two lines 31, 32, to the pump housing 10 and to an impeller blade 11. Both the housing 10 and the impeller blade can, for example, comprise an at least partly conductive material or can be coated with such a material so that the circuit is closed over the lines 31, 32, over the sensor 29 and between the impeller blade 11 and the pump housing 10 as soon as the impeller blade 11 contacts the housing 10.

In this case it would be signaled that the pump is not in the operating state.

As soon as the contact between the impeller blade 11 and the housing 10 is cancelled, the detection device signals the reaching of the expanded state.

FIG. 12 represents a resistance monitoring of a closed wire ring 33 which is spanned around a compressed pump 10. If the wire tears on the expansion of the pump, the resistance in the ring is doubled since one of the current paths is interrupted. This is registered by the sensor 29 and the expanded state is signaled accordingly.

FIG. 13 shows a similar device to FIG. 12 with a ring conductor 34 which is interrupted between the feed lines 35, 36 and which is integrated, for example, into a closed insulation ring. If the insulation ring breaks at a point at which the ring conductor 34 extends, the current path is interrupted by the ring conductor, which is registered by the sensor 29.

FIG. 14 shows a similar apparatus to FIG. 13 with a compressed pump 10, with the current circuit of the ring conductor 33a, however, unlike in FIG. 13, first being open in the transport state and being closed in the expanded state of the pump, that is, in the operating state. The advantage of this variant lies in the fact that the expanded state is only indicated when the ring conductor itself has no defect. In the embodiment in accordance with FIG. 13, a defective ring conductor, interrupted unintentionally, would possibly also indicate the reaching of the expanded state when this has not (yet 1 been reached. In an embodiment in accordance with FIG. 14, this would not be necessary, which provides additional security against malfunction.

FIG. 15 shows the pump 10 with the apparatus from FIG. 14 in the expanded state with a closed ring conductor 33b.

FIG. 16 shows an apparatus similar to that in FIG. 10 in the transport state, but configured so that a switch 37 is arranged at the proximal end of the catheter 38. In this respect, the length of the catheter 38 in relation to the length of the hollow catheter 39 is dimensioned so that the pump head 40 has already fully adopted the expanded state (that is has left the hollow catheter 39) when the proximal end 41 of the hollow catheter 39 actuates the switch 37 (cf. FIG. 17) To avoid unwanted triggering of the switch 37, it is advantageously configured or arranged so that a triggering of the switch is not possible manually during the manipulation. The switch 37 can be arranged outside a patient's body with a sufficient length of the Catheters 38, 39.

FIG. 17 shows the apparatus of FIG. 16 in the operating state.

In FIG. 17, an optical monitoring device is also shown by way of example for the expanded state supplemented with a proximal light source 100, a prism/beam splitter 102, a light guide 103 and an optical sensor 101. The light guide is conducted up to the pump head, conducts light of the light source 100 to there and conducts reflected light back to the optical sensor 101 depending on the compressed or expanded state.

The described invention serves to increase the operating security of compressible pumps and in particular to lower health risks in the medical sector.

The invention claimed is:

1. An intravascular pump device, comprising:
    a first catheter having a proximal end and a distal end;
    a pump head disposed at the distal end of the first catheter, the pump head having a compressed state and an expanded state, wherein the pump head is configured to be positioned across a heart valve and to automatically elastically expand into the expanded state upon release from the first catheter;
    a rotor disposed in the pump head, the rotor having impeller blades, the impeller blades being elastically compressible and configured to automatically elastically expand, wherein the impeller blades are configured to convey a fluid by a supplied energy;
    a flexible shaft coupled at a distal end to the rotor of the pump head;
    a drive comprising a motor configured to drive the flexible shaft, wherein the flexible shaft delivers energy to the rotor; and
    a detection device, comprising:
        a sensor configured to detect a load of the energy supply device by measuring current flowing through the drive and produce an output signal indicative of the detected load;
        a processor configured to:
            receive the output signal;
            calculate the load from the output signal;
            compare the calculated load to a reference value; and
            determine a difference between the calculated load and the reference value based on the comparison; and
        a switch configured to switch off the drive based on the comparison.

2. The pump device of claim 1, wherein the switch is configured to limit the current of the motor.

3. The pump device of claim 2, wherein the switch is configured to block transmission of torque via the flexible shaft when triggered.

4. The pump device of claim 3, wherein in response to the switch being triggered, the detection device emits a warning signal that the pump may not be operable.

5. The pump device of claim 4, wherein the switch is an electric switch.

6. The pump device of claim 4, wherein the switch is a pneumatic switch.

7. The pump device of claim 4, wherein the switch is a coupling.

8. The pump device of claim 1, wherein the sensor is arranged at the pump head.

9. The pump device of claim 1, wherein the sensor is arranged proximal of the pump head.

10. The pump device of claim 1, wherein the sensor is arranged remote from the pump.

11. The pump device of claim 10, wherein the sensor is arranged in the proximity of the flexible shaft.

12. The pump device of claim 1, wherein the detected load is higher when the pump head is not in the expanded state than when the pump head is in the expanded state.

13. The pump device of claim 12, wherein the determined difference between the calculated load and the reference value represents whether the pump head is in the expanded state.

14. The pump device of claim 1, wherein the detection device is configured to detect that an element of the pump has reached an operating state.

15. The pump device of claim 14, wherein the element includes the impeller blades.

16. The pump device of claim 15, wherein the impeller blades comprise an elastic material.

17. The pump device of claim 14, wherein the element is a pump housing.

18. The pump device of claim 1, wherein the detection device blocks the flexible shaft as long as the expanded state is not reached.

19. The pump device of claim 1, further comprising a second catheter surrounding the flexible shaft, wherein the second catheter is configured to move through the first catheter.

20. The pump device of claim 19, wherein the first catheter is configured to compress the pump head when the pump head is inserted into the first catheter.

* * * * *